United States Patent
Travan et al.

(10) Patent No.: US 11,740,199 B2
(45) Date of Patent: Aug. 29, 2023

(54) GAS SENSING DEVICE WITH A GAS FILTER

(71) Applicant: Infineon Technologies AG, Neubiberg (DE)

(72) Inventors: Caterina Travan, Munich (DE); Alexandra Marina Roth, Neumarkt (DE)

(73) Assignee: Infineon Technologies AG, Neubiberg (DE)

( * ) Notice: Subject to any disclaimer, the term of this patent is extended or adjusted under 35 U.S.C. 154(b) by 0 days.

(21) Appl. No.: 17/643,653

(22) Filed: Dec. 10, 2021

(65) Prior Publication Data

US 2022/0236207 A1 Jul. 28, 2022

(30) Foreign Application Priority Data

Jan. 22, 2021 (EP) .................................... 21153058

(51) Int. Cl.
*G01N 27/12* (2006.01)
*G01N 33/00* (2006.01)

(52) U.S. Cl.
CPC ....... *G01N 27/128* (2013.01); *G01N 33/0014* (2013.01)

(58) Field of Classification Search
CPC .. G01N 27/128; G01N 33/0014; G01N 27/12; G01N 27/125; G01N 27/127; C01B 32/158

See application file for complete search history.

(56) References Cited

U.S. PATENT DOCUMENTS

| | | | |
|---|---|---|---|
| 10,012,639 B1* | 7/2018 | Azimi | G01N 33/4972 |
| 2015/0256917 A1* | 9/2015 | Schelling | H04R 1/04 381/111 |
| 2017/0276634 A1* | 9/2017 | Saffell | G01N 27/40 |
| 2018/0135287 A1 | 5/2018 | Hall et al. | |
| 2020/0064291 A1* | 2/2020 | Varganov | B01J 31/1691 |

FOREIGN PATENT DOCUMENTS

| | | |
|---|---|---|
| EP | 2533037 A1 | 12/2012 |
| JP | H10123083 A | 5/1998 |
| WO | 2013008170 A2 | 1/2013 |

\* cited by examiner

*Primary Examiner* — Feba Pothen
(74) *Attorney, Agent, or Firm* — Slater Matsil, LLP

(57) ABSTRACT

A gas sensing device includes chemoresistive gas sensing elements, wherein a material composition of a first chemoresistive gas sensing element is similar to a material composition of a second chemoresistive gas sensing element, wherein the first chemoresistive gas sensing element is exposed to an ambient mixture of gases so that first sensing signals depend on a concentration of a first gas and on a concentration of a second gas, wherein the gas sensing device includes a gas filter so that the second sensing signals depend on the concentration of the first gas to a lesser degree than the first sensor signals and so that the second sensing signals depend on the concentration of the second gas, and wherein the gas sensing device estimates the concentration of the first gas and/or the concentration of the second gas based on the first sensing signals and the second sensing signals.

9 Claims, 8 Drawing Sheets

GAS SENSING DEVICE WITH A GAS FILTER

CROSS-REFERENCE TO RELATED APPLICATIONS

This application claims the benefit of European Patent Application No. 21153058, filed on Jan. 22, 2021, which application is hereby incorporated herein by reference.

TECHNICAL FIELD

The disclosure relates to gas sensing devices, in particular to chemoresistive gas sensing devices for sensing different gases in an ambient mixture of gases.

BACKGROUND

Chemoresistive sensing devices of sensing different gases are known in the art. However, there is a need for improving the accuracy of the sensing results of such sensing devices.

SUMMARY

The problem is solved by a gas sensing device for sensing a first gas and at least one second gas in an ambient mixture of gases;
wherein the gas sensing device comprises a plurality of chemoresistive gas sensing elements, wherein a first chemoresistive gas sensing element of the plurality of chemoresistive gas sensing elements is configured for providing first sensing signals, and wherein a second chemoresistive gas sensing element of the plurality of chemoresistive gas sensing elements is configured for providing second sensing signals;
wherein a material composition of the first chemoresistive gas sensing element is similar to a material composition of the second chemoresistive gas sensing element, wherein the material composition is suitable for sensing the first gas and the at least one second gas;
wherein the first chemoresistive gas sensing element is exposed to the ambient mixture of gases so that the first sensing signals depend on a concentration of the first gas in the ambient mixture of gases and on a concentration of the second gas in the ambient mixture of gases;
wherein the gas sensing device comprises a gas filter, which is less permeable for the first gas than for the at least one second gas, wherein the gas filter is arranged in such way that the second chemoresistive gas sensing element is exposed to a filtered mixture of gases obtained by filtering the ambient mixture of gases with the gas filter so that the second sensing signals depend on the concentration of the first gas in the ambient mixture of gases to a lesser degree than the first sensor signals and so that the second sensing signals depend on the concentration of the second gas in the ambient mixture of gases;
wherein the gas sensing device is configured for estimating the concentration of the first gas in the ambient mixture of gases and/or the concentration of the second gas in the ambient mixture of gases based on the first sensing signals and based on the second sensing signals.

In general, a chemoresistive gas sensing element is an electronic component that changes its electrical resistance in response to changes of the concentrations of nearby gases. The gases, for which a chemoresistive gas sensing element is sensitive, depend on the material composition of the chemoresistive gas sensing element. One problem lies in that most of the suitable material compositions interact with more than one gas, which is also known as cross-sensitivity, so that it is demanding to distinguish the influence of different gases in a mixture of gases on the electrical resistance of the chemoresistive gas sensing element.

The proposed gas sensing device comprises at least a first chemoresistive gas sensing element for producing first sensing signals and the second chemoresistive gas sensing element for producing second sensing signals, wherein the material composition of both chemoresistive gas sensing elements is similar control and in such way that the material composition is sensitive to at least a first gas and the second gas. Each of the gas sensing elements may be manufactured as a microelectromechanical system (MEMS). The two sensing elements may have similar dimensions and may be arranged inside a common package.

The first chemoresistive gas sensing element is arranged in such way, that it is exposed to an ambient mixture of gases comprising at least the first gas and the second gas. In contrast to that, the second chemoresistive gas sensing element is arranged in such way that it is exposed to a filtered mixture of gases which is obtained by filtering the ambient mixture of gases, wherein the gas filter is used which is impermeable for the first gas and permeable for the second gas.

In this way, it ensured that the first sensing signals depend on a concentration of the first gas in the ambient mixture of gases and on a concentration of the second gas in the ambient mixture of gases. Moreover, it ensured that the second sensing signals do not depend on the concentration of the first gas in the ambient mixture of gases, or at least to a lesser degree than the first sensor signals. However, that the second sensing signals depend on the concentration of the second gas in the ambient mixture of gases.

The gas sensing device estimates the concentration of the first gas in the ambient mixture of gases and/or the concentration of the second gas in the ambient mixture of gases by taking into account the first sensing signals and the second sensing signals simultaneously.

The gas sensing device may comprise a processing device comprising a gas concentration estimator, wherein the first sensing signals and the second sensing signals are fed to the gas concentration estimator, wherein the gas concentration estimator is configured for estimating the concentration of the first gas in the ambient mixture of gases and/or the concentration of the second gas in the ambient mixture of gases based on the first sensing signals and based on the second sensing signals.

Both of the sensing elements may be controlled by the same processing device.

In some embodiments, the processing device comprises hardware only. In other embodiments, the processing device comprises hardware and software. In particular, the processing device may comprise an application-specific integrated circuit (ASIC) and/or a microcontroller.

The gas concentration estimator may comprise the lookup table to which values of the first sensing signals and corresponding values of the second sensing signals are fed to, and which outputs values for a concentration of the first gas and values for concentration of the second gas. The content of the lookup table may be determined experimentally.

The combination of the first chemoresistive sensing element, the second chemoresistive sensing element, the gas filter and the estimation of the gas concentrations by assessing simultaneously the first sensor signals and the second sensor signals ensures that the cross-sensitivity of the proposed gas sensing device is significantly lower than the cross-sensitivity of pre-known multi-gas sensors.

The gas sensing device according to the disclosure is, in particular, suitable for air quality monitoring in outdoor applications. It may be produced at low costs, may have small dimensions and may have a low power consumption.

According to some embodiments, the second chemoresistive gas sensing element is arranged in an enclosed containment, wherein the gas filter is implemented as a portion of a wall structure of the enclosed containment. These features are especially advantages, if the material of the gas filter does not allow attaching the gas filter directly to the second chemoresistive gas sensing element. Using an enclosed containment ensures that the second chemoresistive gas sensing element is prevented from getting into contact with the first gas.

According to some embodiments, the first gas is ozone. According to some embodiments, the at least one second gas comprises nitrogen dioxide. Ozone and nitrogen dioxide cause a very similar reaction on chemoresistive gas sensing elements. Thus, prior art chemoresistive gas sensor devices are not able to separate completely the contribution of the two gases to the eventual value of the electrical resistance of the chemoresistive gas sensing element, as both gases are oxidizing gases with similar binding energy causing a similar change in the electrical resistance of the chemoresistive sensing element. However, at the disclosed solution data the processing device use the information coming from the two sensor elements (one exposed just to ozone and the other exposed to nitrogen dioxide and ozone) to differentiate between the two gases so that it is possible to predict the concentration of each of them with high accuracy.

According to some embodiments, the material composition of the first chemoresistive gas sensing element and of the second chemoresistive gas sensing element comprises a mixed oxide (MOX) or materials comprising carbon like e.g. graphene, carbon nanotubes etc. Such materials are suitable for gas sensing devices, however with materials shows strong cross-sensitivity when exposed to nitrogen dioxide and ozone so that it is very demanding to separate properly the contribution of the two gases to the value of the electrical resistance of the gas sensing element comprising these materials. However, the proposed gas sensing device is capable of measuring correctly the concentration of each of the two gases.

According to some embodiments, the gas sensing device comprises a processing device comprising a gas concentration estimator comprising a trained model based algorithm processor having an input layer and an output layer, wherein first sensing data derived from the first sensing signals and second sensing data derived from the second sensing signals are fed simultaneously to the input layer, and wherein the concentration of the first gas in the ambient mixture of gases and/or the concentration of the second gas in the ambient mixture of gases are estimated based on output data of the output layer.

A trained model based algorithm processor is a processor, which is capable of machine learning. The machine learning is done in a preoperational training phase in which trained models are developed by comparing actual output values of the trained model based algorithm stage with desired output values of the trained model based algorithm stage for defined inputs of the trained model based algorithm stage. The trained models have a predefined structure, wherein a parametrization of the predefined structure is done during the training phase. The trained models comprise the learned content after the training phase is finished. In an operational phase for producing sensing results one or more of the trained models from the training phase are used to process the first sensing data and the second sensing data.

In the training phase, a plurality of trained models can be established and afterwards stored at the processing device or alternatively on a software running on an external microcontroller. The trained models may differ in the structures and/or the parameters. During an operational phase, the most appropriate trained model may be selected depending on the specific use-case.

The use of a trained model based algorithm processor (in contrast to the use of a look-up table) ensures, that in an operational phase also input values, which were not used in a pre-operational experimental or training phase, are processed in such way that a measurement error is minimized.

According to some embodiments, the first chemoresistive gas sensing element, the second chemoresistive gas sensing element and the processing device are arranged at a common substrate. By these features, the dimensions of the gas sensing device and the manufacturing effort may be minimized. The common substrate maybe made, in particular, of a semiconductor material.

According to some embodiments, the first chemoresistive gas sensing element and the second chemoresistive gas sensing element are arranged in an enclosed housing, wherein a wall structure of the enclosed housing comprises a particle filter, which is impermeable for particles and permeable for the first gas and for the at least one second gas. By these features, clogging of the gas sensitive areas of the two gas sensing elements by particles may be prevented.

According to some embodiments, the gas filter is implemented as a coating of a gas-sensitive area of the second chemoresistive gas sensing element. The coating may, e.g., comprise manganese oxide ($MnO_2$). By these features, the dimensions of the gas sensing device and the manufacturing effort may be further minimized.

According to some embodiments, the gas sensing device comprises a first heating device configured for heating the first chemoresistive gas sensing element and a second heating device configured for heating the second chemoresistive gas sensing element, wherein the processing device comprises a heat control device configured for controlling the first heating device according to a first temperature profile and for controlling the second heating device according to a second temperature device, wherein a maximum temperature of the first temperature profile is lower than a maximum temperature of the second temperature profile.

In general, the exposure to very high concentrations of oxidizing gases, such as ozone, using high operating temperatures can damage, depending on the sensing material, the chemoresistive gas sensing elements and using low operating temperature causes a slow response and recovery of the chemoresistive gas sensing elements. Vice versa, the usage of a low operation temperature reduces the damage of the chemoresistive sensor elements in presence of oxidizing gases, such as ozone, however a very low operation temperature is limiting the sensor performance since it causes a slow sensor response and its subsequent recovery.

As the second chemoresistive gas sensing element of the proposed gas sensing device is prevented from contact with one of the gases, the operational temperatures of the second chemoresistive gas sensing element may be chosen higher than the operational temperatures of the first chemoresistive gas sensing element, in case that the respective gas is an oxidizing gases such as ozone. In this way, the response and the recovery of the second chemoresistive gas sensing element can be drastically enhanced.

According to some embodiments, the first chemoresistive gas sensing element and the second chemoresistive gas sensing element are arranged at a common side of the common substrate, wherein the processing device is arranged at an opposite side of the common substrate, wherein the first chemoresistive gas sensing element and the second chemoresistive gas sensing element are electrically connected to the processing device by vias. By these features, the dimensions of the gas sensing device and the manufacturing effort may be further minimized.

BRIEF DESCRIPTION OF THE DRAWINGS

Preferred embodiments of the invention are subsequently discussed with respect to the accompanying drawings, in which.

Figure 1:
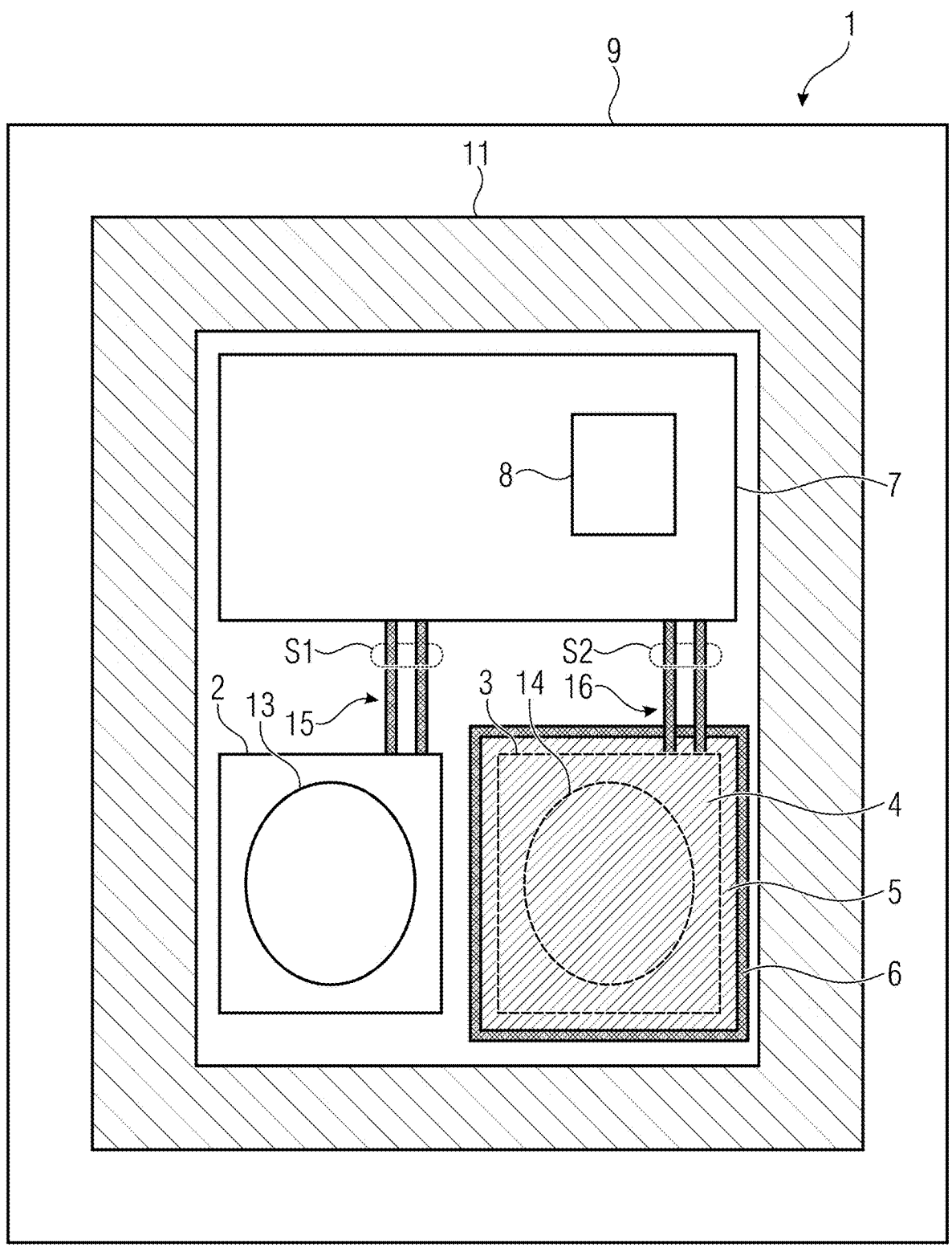
FIG. 1 illustrates a first embodiment of a gas sensing device according to the disclosure in a schematic cross-sectional top view.

Equal or equivalent elements or elements with equal or equivalent functionality are denoted in the following description by equal or equivalent reference numerals.

DETAILED DESCRIPTION OF ILLUSTRATIVE EMBODIMENTS

Figure 2:
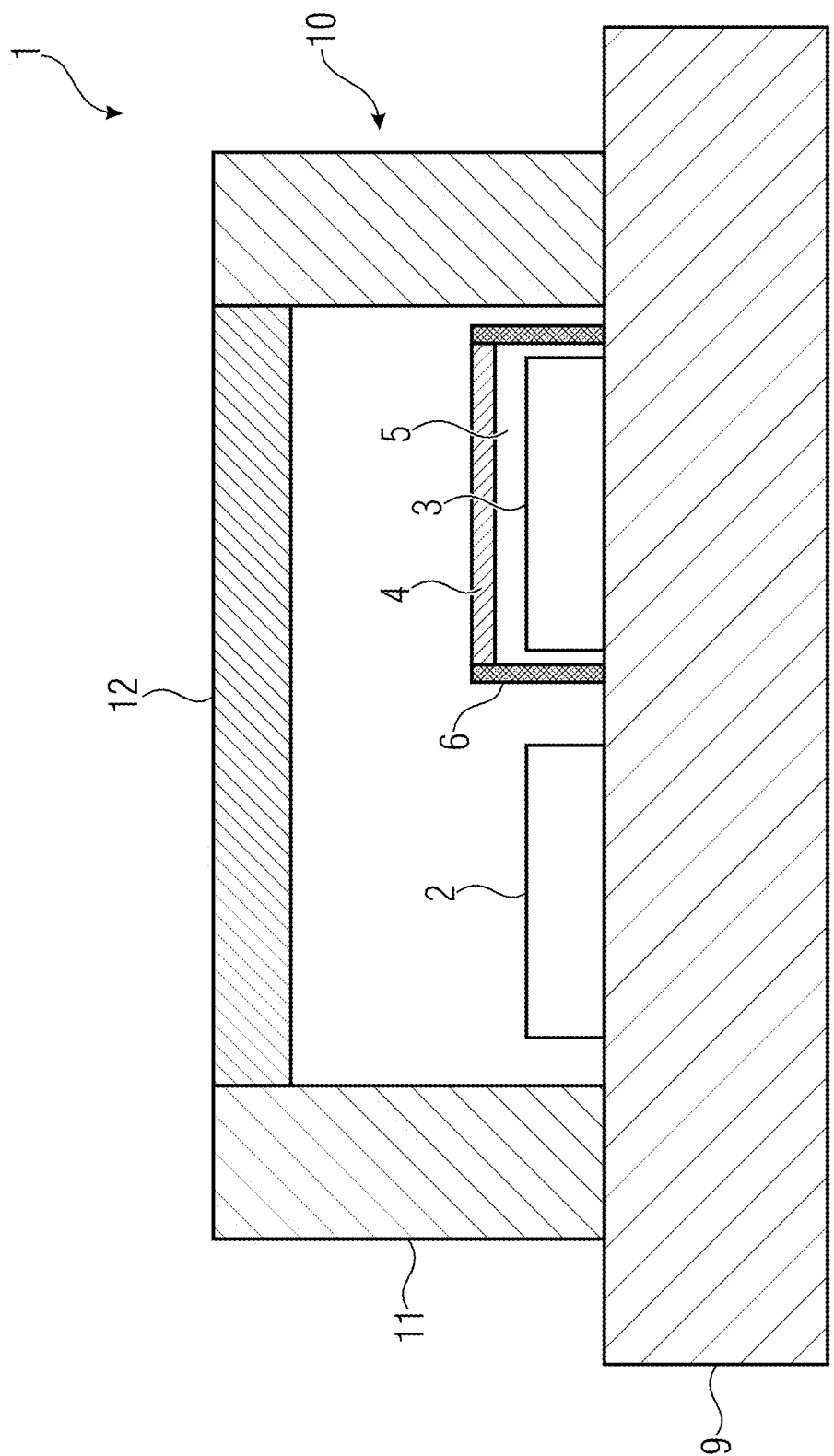
FIG. 2 illustrates the first embodiment of a gas sensing device according to the disclosure in a schematic cross-sectional side view.

FIG. 1 illustrates a first embodiment of a gas sensing device 1 according to the disclosure in a schematic cross-sectional top view and FIG. 2 illustrates the first embodiment of a gas sensing device 1 according to the disclosure in a schematic cross-sectional side view.

Disclosed is a gas sensing device for sensing a first gas and at least one second gas in an ambient mixture of gases;

wherein the gas sensing device 1 comprises a plurality of chemoresistive gas sensing elements 2, 3, wherein a first chemoresistive gas sensing element 2 of the plurality of chemoresistive gas sensing elements 2,3 is configured for providing first sensing signals S1, and wherein a second chemoresistive gas sensing element 3 of the plurality of chemoresistive gas sensing elements 2, 3 is configured for providing second sensing signals S2;

wherein a material composition of the first chemoresistive gas sensing element 2 is similar to a material composition of the second chemoresistive gas sensing element 3, wherein the material composition is suitable for sensing the first gas and the at least one second gas;

wherein the first chemoresistive gas sensing element 2 is exposed to the ambient mixture of gases so that the first sensing signals S1 depend on a concentration of the first gas in the ambient mixture of gases and on a concentration of the second gas in the ambient mixture of gases;

wherein the gas sensing device 1 comprises a gas filter 4, which is less permeable for the first gas than for the at least one second gas, wherein the gas filter 4 is arranged in such way that the second chemoresistive gas sensing element 3 is exposed to a filtered mixture of gases obtained by filtering the ambient mixture of gases with the gas filter 4 so that the second sensing signals S2 depend on the concentration of the first gas in the ambient mixture of gases to a lesser degree than the first sensor signals S1 and so that the second sensing signals 2 depend on the concentration of the second gas in the ambient mixture of gases;

wherein the gas sensing device 1 is configured for estimating the concentration of the first gas in the ambient mixture of gases and/or the concentration of the second gas in the ambient mixture of gases based on the first sensing signals S1 and based on the second sensing signals S2.

According to some embodiments, the second chemoresistive gas sensing element 3 is arranged in an enclosed containment 5, wherein the gas filter 4 is implemented as a portion of a wall structure 6 of the enclosed containment 5.

In the example of FIGS. 1 and 2, the enclosed containment 5 is formed by the gas filter 4, the wall structure 6 and the common substrate 9.

According to some embodiments, the first gas is ozone.

According to some embodiments, the at least one second gas comprises nitrogen dioxide.

According to some embodiments, the material composition of the first chemoresistive gas sensing element 2 and of the second chemoresistive gas sensing element 3 comprises a mixed oxide or materials comprising carbon like e.g. graphene, carbon nanotubes etc.

According to some embodiments, the gas sensing device 1 comprises a processing device 7 comprising a gas concentration estimator 8 comprising a trained model based algorithm processor having an input layer and an output layer, wherein first sensing data derived from the first sensing signals S1 and second sensing data derived from the second sensing signals S2 are fed simultaneously to the input layer, and wherein the concentration of the first gas in the ambient mixture of gases and/or the concentration of the second gas in the ambient mixture of gases are estimated based on output data of the output layer.

According to some embodiments, the first chemoresistive gas sensing element 2, the second chemoresistive gas sensing element and the processing device 7 are arranged at a common substrate 9.

According to some embodiments, the first chemoresistive gas sensing element 2 and the second chemoresistive gas sensing element 3 are arranged in an enclosed housing wherein a wall structure 11 of the enclosed housing 10 comprises a particle filter 12, which is impermeable for particles and permeable for the first gas and for the at least one second gas.

In the example of FIGS. 1 and 2, the enclosed housing 10 is formed by the common substrate 9, the wall structure 11 and the particle filter 12.

In the example of FIGS. 1 and 2, the first chemoresistive gas sensor element 2 comprises one gas sensitive area 13 and the second chemoresistive gas sensor element 3 comprises one gas sensitive area 14. The first sensing signals S1 are transmitted over first electrical connectors 15 from the first chemoresistive gas sensing element 2 to the processing device 7. Similarly, the second sensing signals S2 are transmitted over second electrical connectors 16 from the second chemoresistive gas sensing element 3 to the processing device 7.

In the example of FIGS. 1 and 2, the gas sensing device 1 comprises two chemoresistive gas sensing elements 2, 3 with the same type of material composition and controlled by the same processing device 7. Each of the chemoresistive gas sensing elements 2, 3 has one or multiple gas sensing areas 13, 14. All the chemoresistive gas sensing elements 2, 3 are located inside the same package and one (or more) of the chemoresistive gas sensing elements 2, 3 is protected by a gas filter 4, which filters out ozone. The two (or more) chemoresistive gas sensing elements 2, 3 can be on different microelectromechanical systems and then the chemoresistive gas sensing element 3 with the gas filter 4 will have an enclosed containment 5 with a wall structure 6 (e.g. a small lid with a big opening) that will mechanically support the gas filter for on top. The chemo resistive gas sensing element 2 without the gas filter 4 will react to nitrogen dioxide and ozone and should be operated at a temperature low enough in order to avoid oxidation of the material due to the presence of ozone. The chemoresistive gas sensing element 3 with the gas filter 4 will not react to ozone and, therefore, is sensitive for nitrogen dioxide only.

Figure 3:
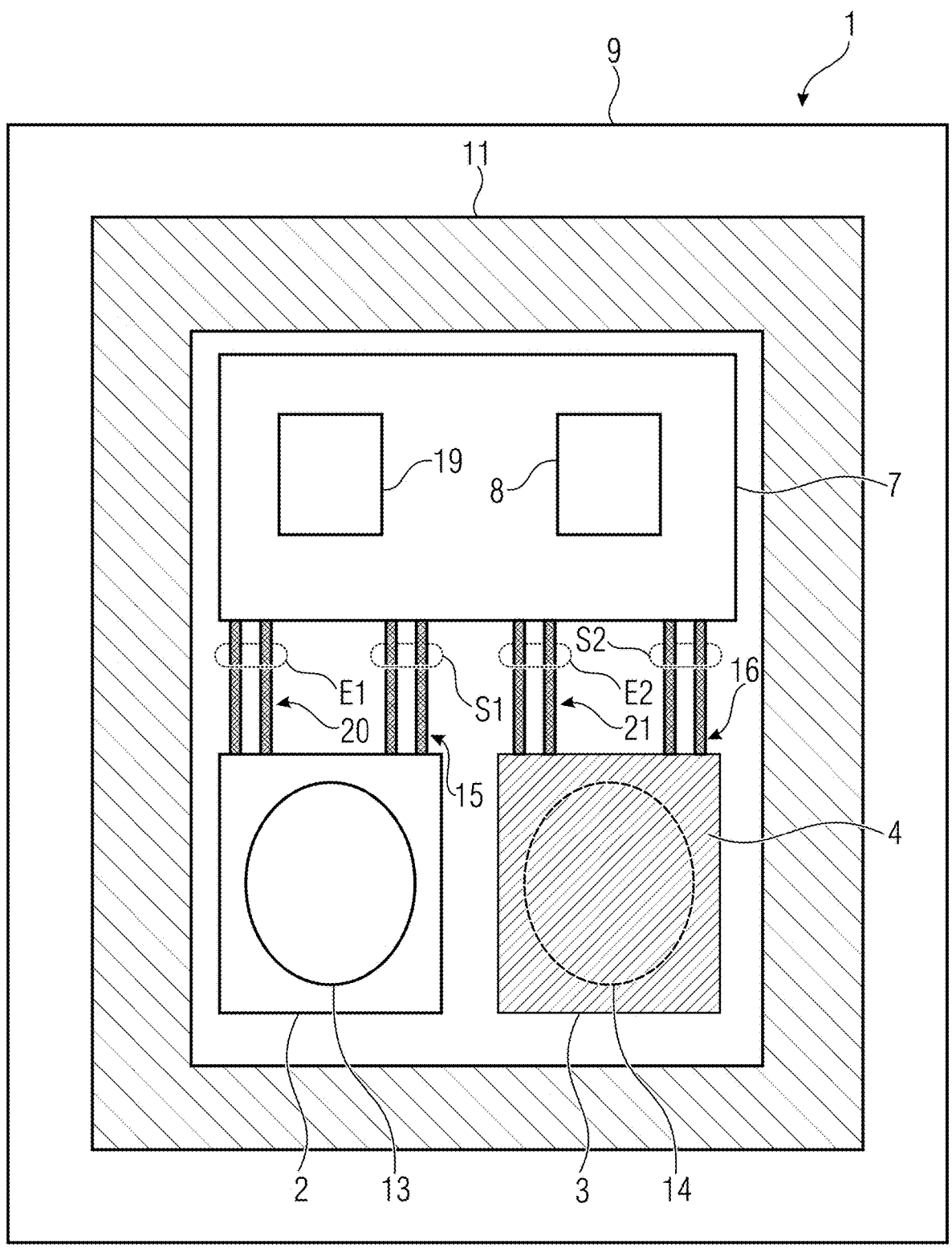
FIG. 3 illustrates a second embodiment of a gas sensing device according to the disclosure in a schematic cross-sectional top view.
Figure 4:
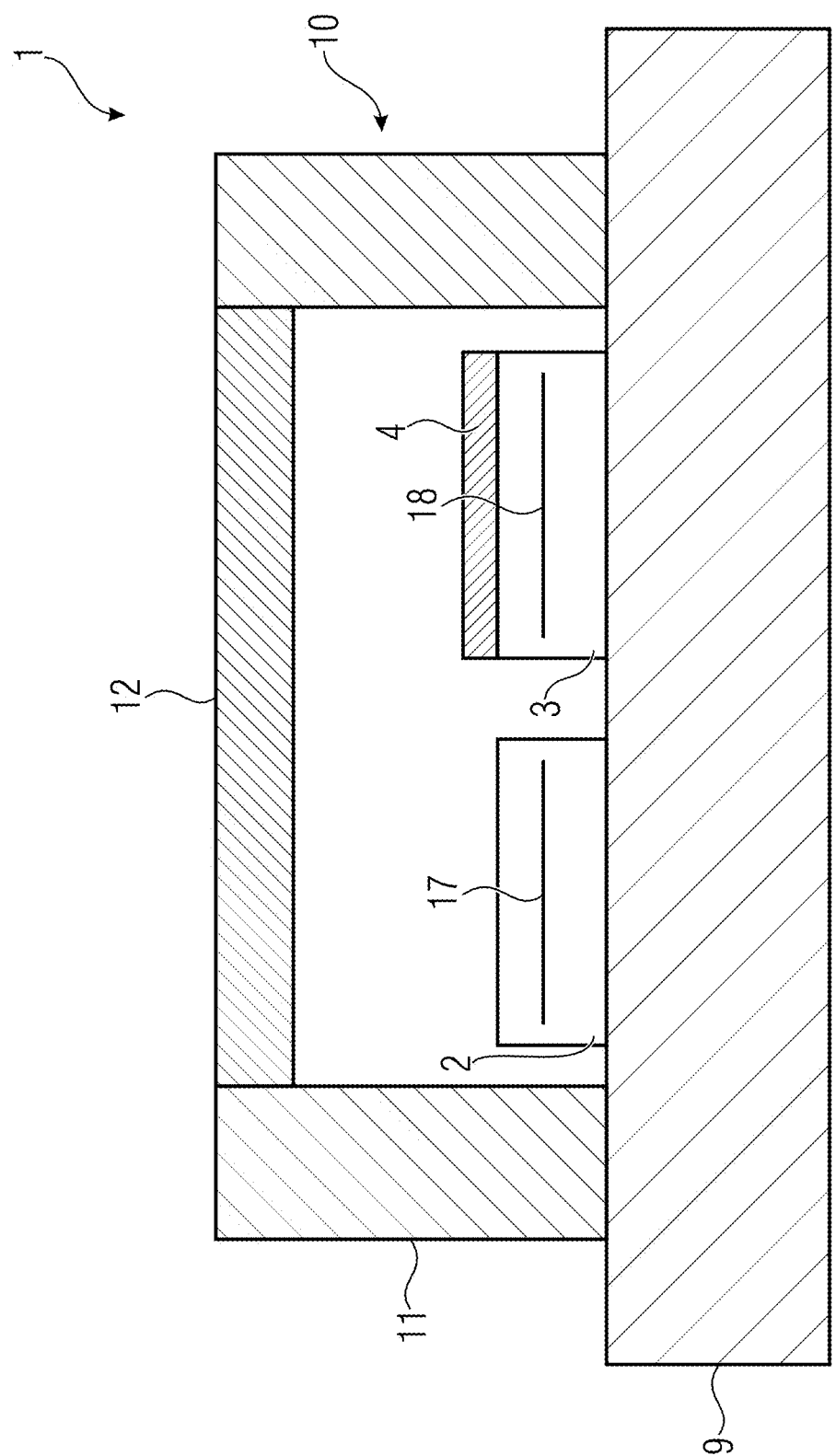
FIG. 4 illustrates the second embodiment of a gas sensing device according to the disclosure in a schematic cross-sectional side view.

FIG. 3 illustrates a second embodiment of a gas sensing device 1 according to the disclosure in a schematic cross-sectional top view and FIG. 4 illustrates the second embodiment of a gas sensing device 1 according to the disclosure in a schematic cross-sectional side view.

According to some embodiments, the gas filter 4 is implemented as a coating of a gas-sensitive area 14 of the second chemoresistive gas sensing element 3.

According to some embodiments, the gas sensing device 1 comprises a first heating device 17 configured for heating the first chemoresistive gas sensing element 2 and a second heating device 18 configured for heating the second chemoresistive gas sensing element 3, wherein the processing device 7 comprises a heat control device 19 configured for controlling the first heating device 17 according to a first temperature profile and for controlling the second heating device 18 according to a second temperature device, wherein a maximum temperature of the first temperature profile is lower than a maximum temperature of the second temperature profile.

In the example of FIGS. 3 and 4, the first chemoresistive gas sensing element 2 is heated by a first heating device 17 and the second chemoresistive gas sensing element 3 is heated by a second heating device 18. The processing device 7 comprises a heat control device 19, which supplies a first electrical energy E1 over third electrical connectors 22 the first heating device 17, and which supplies second electrical energy E2 over the fourth electrical connectors 23 to the second heating device 18. By these features, an operational temperature of the first chemoresistive gas sensing element 2 may be controlled independently from an operational temperature of the second chemoresistive gas sensing element 3. In other embodiments, a common heating device could be used for heating both of the gas sensing elements 2, 3.

In the example of FIGS. 3 and 4, both gas sensing elements 2, 3 are arranged on a common microelectromechanical system. The gas sensing element 3 has a layer of material which catalyzes the ozone decomposition (e.g. $MnO_2$) deposited or grown on the top of the sensing material.

The gas sensing elements 2, 3 can have independent heating devices 17, 18 or just one heating device.

Figure 5:
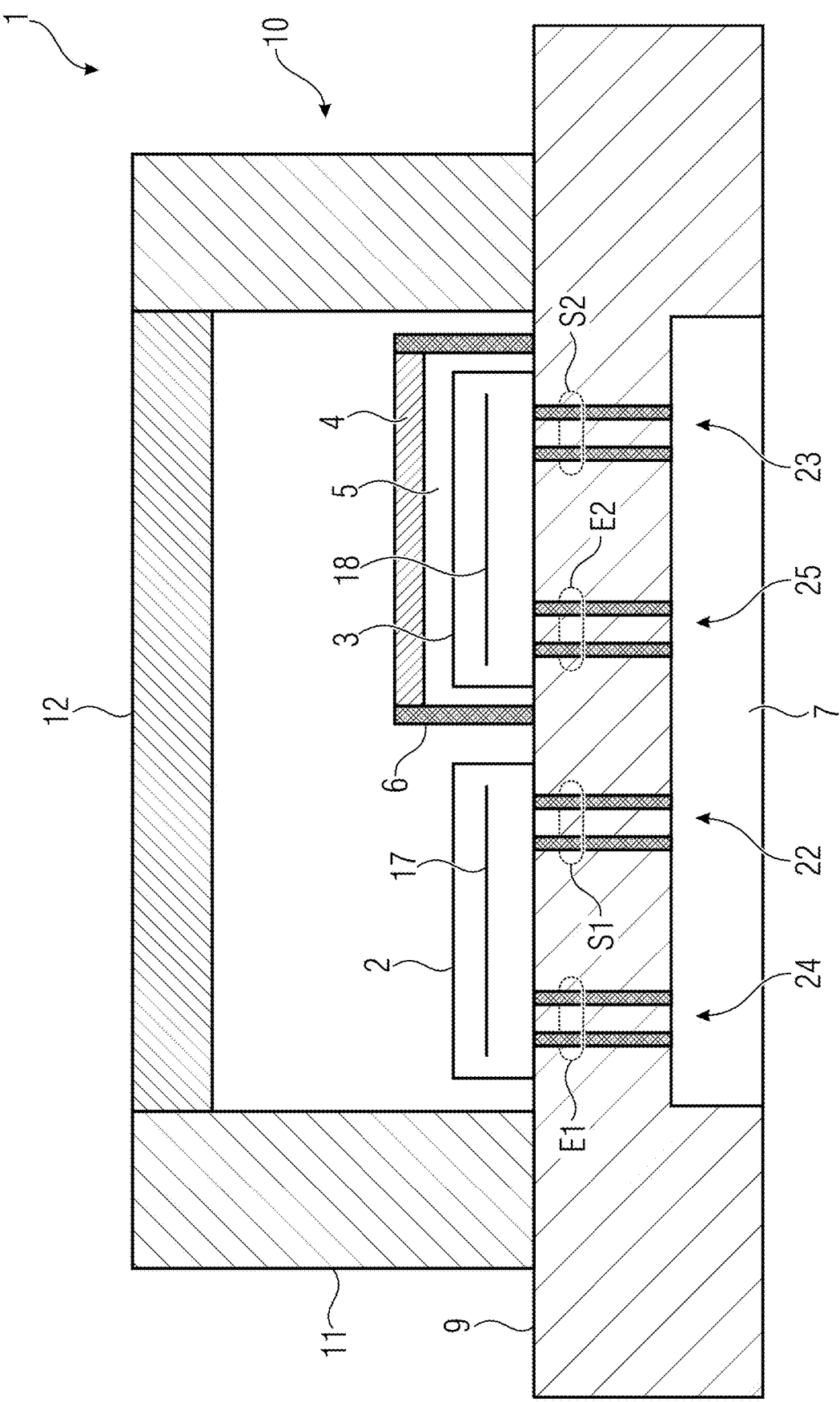
FIG. 5 illustrates the third embodiment of a gas sensing device according to the disclosure in a schematic cross-sectional side view.

FIG. 5 illustrates the third embodiment of a gas sensing device 1 according to the disclosure in a schematic cross-sectional side view.

According to some embodiments, the first chemoresistive gas sensing element 2 and the second chemoresistive gas sensing element 3 are arranged at a common side of the common substrate 9, wherein the processing device 7 is arranged at an opposite side of the common substrate 9, wherein the first chemoresistive gas sensing element 2 and the second chemoresistive gas sensing element 3 are electrically connected to the processing device by vias 22, 23, 24, 25.

In the example of FIG. 5, the first chemoresistive gas sensing element 2 and the second chemoresistive gas sensing element 3 are arranged at a top side of the common substrate 9, wherein the processing device 7 is arranged at a bottom side of the common substrate 9. The first sensing signals S1 are transmitted over a first group of vias 22 to the processing device 7. The second sensing signals are transmitted over a second group of vias 23 to the processing device 7. The first electrical energy E1 is provided to the first heating device 17 using a third group of vias 24. Similarly, the second electrical energy E2 is provided to the second heating device 18 using a fourth group of wires 25.

The gas sensing device 1 could be extended to other gases which cause a similar response in the material composition of the gas sensing elements, using two (or more) second chemoresistive gas sensing elements 3, where one (or more) of the second chemoresistive gas sensing elements 3 is covered with a gas filter for filtering out a first gas of the gases and the other second chemoresistive gas sensing element free (or sensors) has a gas filter for filtering out a further gas of the gases.

Figure 6A:
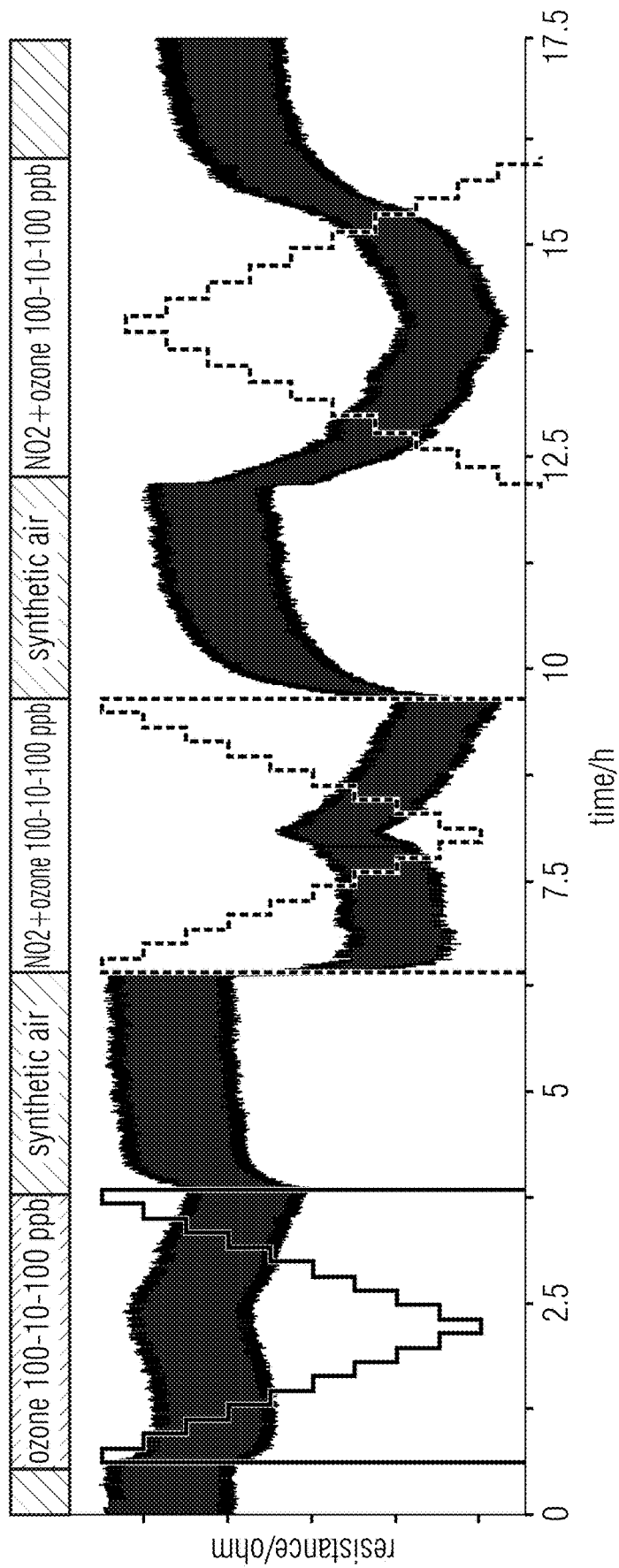
FIGS. 6A and 6B illustrate an exemplary resistance change of a chemoresistive gas sensing element upon applying various concentrations of nitrogen dioxide and ozone with (FIG. 6A) and without (FIG. 6B) a gas filter.
Figure 6B:
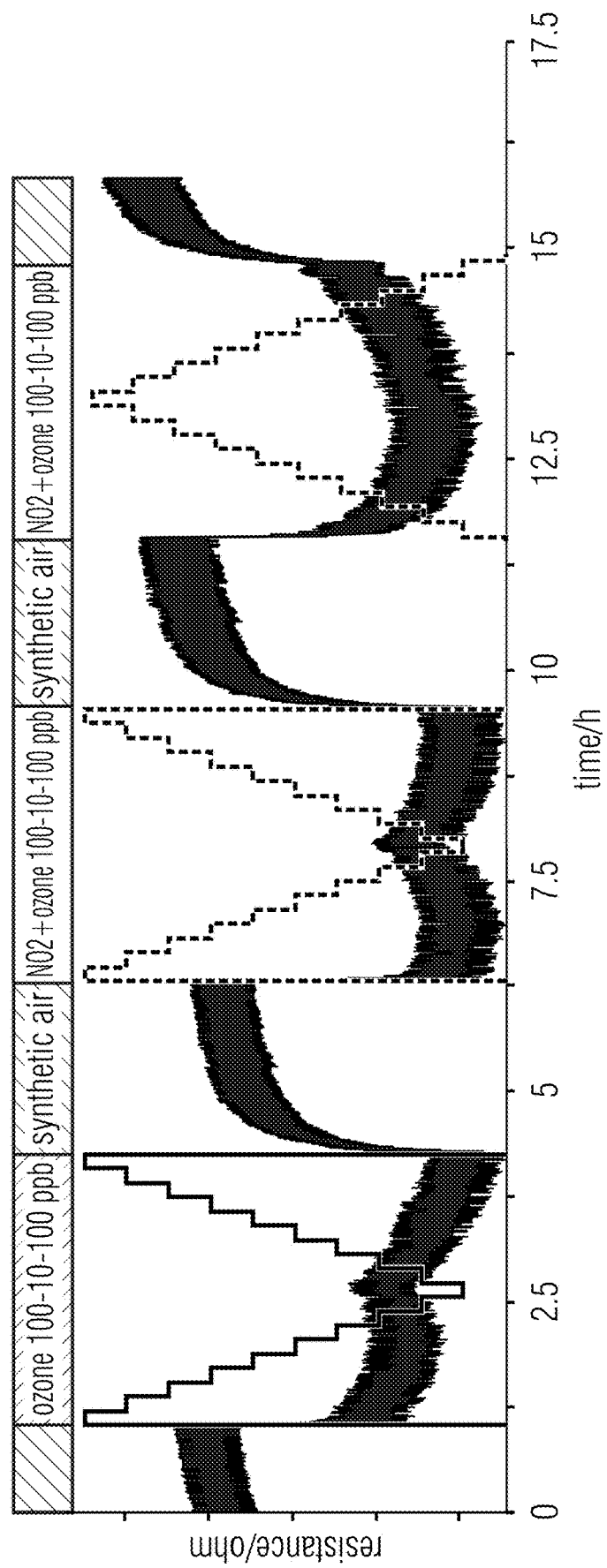

FIGS. 6A and 6B illustrate an exemplary resistance change of a chemoresistive gas sensing element 2, 3 upon applying various concentrations of nitrogen dioxide and ozone with (FIG. 6A) and without (FIG. 6B) a gas filter 4.

The same measurement was done with the same chemoresistive sensing element 2, 3 twice—once without a gas filter 4 and once with a gas filter 4. The gas filter 4 was consisting of a standard filter paper which was impregnated with indigo—a material which decomposes ozone. The sensor response to ozone (measured by a change of the resistance of the gas sensitive area 13, 14) is very low when using a gas filter 4 as can be observed in FIG. 6. Moreover, the recovery of the chemoresistive sensing element 2, 3 is faster and the damage on the chemoresistive sensing element 2, 3 (resistance increase of the baseline resembling an oxidation of the sensing material) is lowered.

Figure 7:
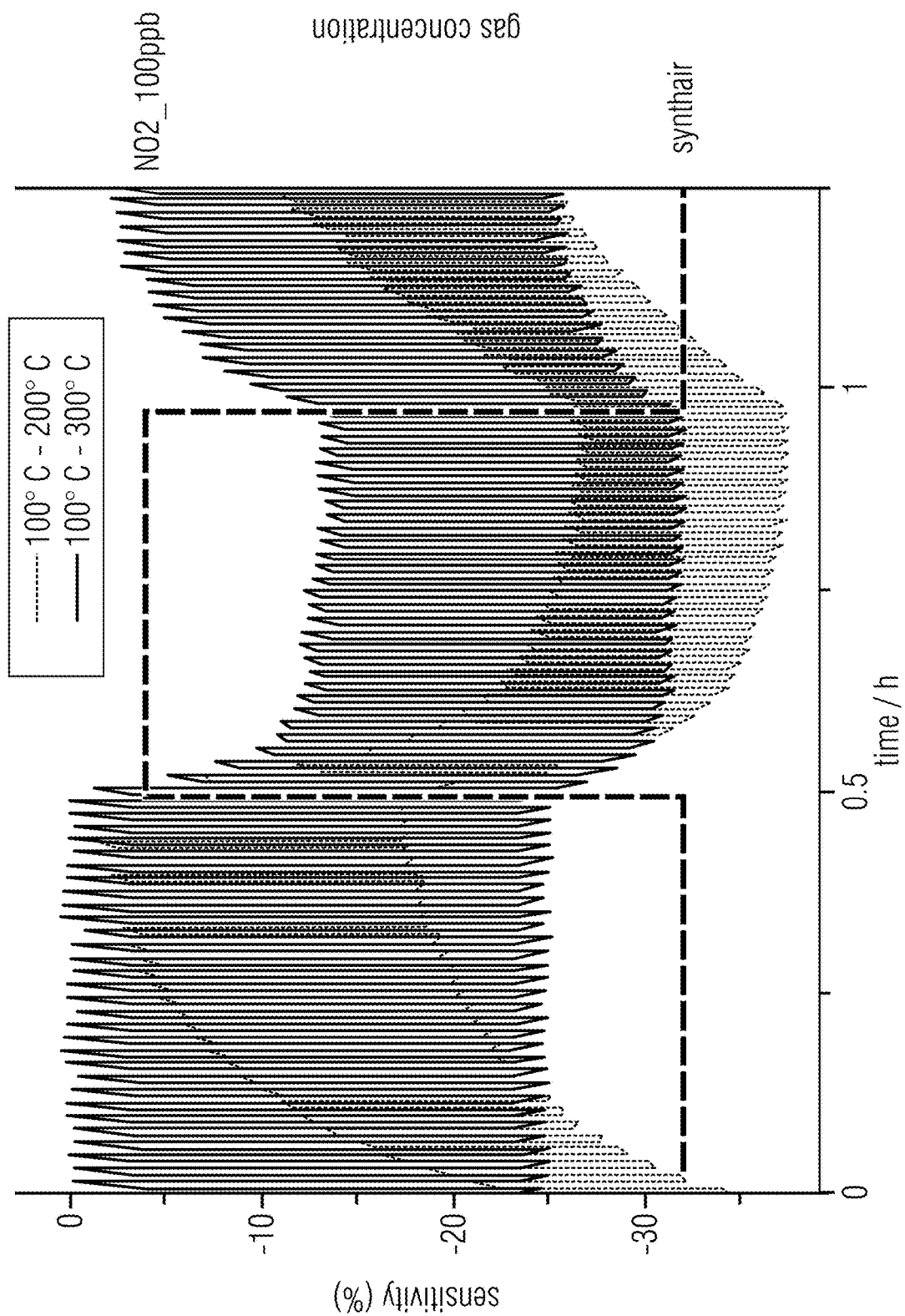
FIG. 7 illustrates an exemplary resistance change of a chemoresistive gas sensing element when applying a certain NO2 concentration measured subsequently with different recovery temperatures.

FIG. 7 illustrates an exemplary resistance change of a chemoresistive gas sensing element 2, 3 when applying a certain NO2 concentration measured subsequently with different recovery temperatures.

When the chemoresistive sensing element 3 is protected from exposure to high concentration of ozone, then a higher operational temperature can be used without damaging the chemoresistive sensing element 3. This would improve the overall sensor performance of the second chemoresistive sensing element 3, thanks to a faster response and recovery and a more stable reaction to gases. The slightly lower sensitivity at higher temperature is not a limitation since the sensitivity is still above the detection limit for the concentration of interest (>20 ppb) of the target gas.

Using 200° C. as recovery temperature results in a more pronounced sensitivity but the response time as well as the recovery time are longer compared to a measurement with 300° C. recovery temperature.

Although some aspects have been described in the context of an apparatus, it is clear that these aspects also represent a description of the corresponding method, where a block or device corresponds to a method step or a feature of a method step. Analogously, aspects described in the context of a method step also represent a description of a corresponding block or item or feature of a corresponding apparatus.

The above described is merely illustrative, and it is understood that modifications and variations of the arrangements and the details described herein will be apparent to others skilled in the art. It is the intent, therefore, to be limited only by the scope of the impending claims and not by the specific details presented by way of description and explanation above.

What is claimed is:

1. A gas sensing device for sensing a first gas and at least one second gas in an ambient mixture of gases;
    wherein the gas sensing device comprises a plurality of chemoresistive gas sensing elements, wherein a first chemoresistive gas sensing element of the plurality of chemoresistive gas sensing elements is configured for providing first sensing signals, and wherein a second chemoresistive gas sensing element of the plurality of chemoresistive gas sensing elements is configured for providing second sensing signals;
    wherein a material composition of the first chemoresistive gas sensing element is similar to a material composition of the second chemoresistive gas sensing element, wherein the material composition is suitable for sensing the first gas and the at least one second gas;
    wherein the first chemoresistive gas sensing element is exposed to the ambient mixture of gases so that the first sensing signals depend on a concentration of the first gas in the ambient mixture of gases and on a concentration of the second gas in the ambient mixture of gases;
    wherein the gas sensing device comprises a gas filter, which is less permeable for the first gas than for the at least one second gas, wherein the gas filter is arranged in such way that the second chemoresistive gas sensing element is exposed to a filtered mixture of gases obtained by filtering the ambient mixture of gases with the gas filter so that the second sensing signals depend on the concentration of the first gas in the ambient mixture of gases to a lesser degree than the first sensing signals and so that the second sensing signals depend on the concentration of the second gas in the ambient mixture of gases; and
    wherein the gas sensing device is configured for estimating the concentration of the first gas in the ambient mixture of gases and/or the concentration of the second gas in the ambient mixture of gases based on the first sensing signals and based on the second sensing signals,
    wherein the second chemoresistive gas sensing element is arranged in an enclosed containment, wherein the gas filter is implemented as a portion of a wall structure of the enclosed containment,
    wherein the first chemoresistive gas sensing element and the second chemoresistive gas sensing element are arranged in an enclosed housing, wherein a wall structure of the enclosed housing comprises a particle filter, which is impermeable for particles and permeable for the first gas and for the at least one second gas, and
    wherein the wall structure of the enclosed containment is between the first chemoresistive gas sensing element and the second chemoresistive gas sensing element.

2. The gas sensing device according to claim 1, wherein the first gas is ozone.

3. The gas sensing device according to claim 1, wherein the at least one second gas comprises nitrogen dioxide.

4. The gas sensing device according to claim 1, wherein the material composition of the first chemoresistive gas sensing element and of the second chemoresistive gas sensing element comprises a mixed oxide or materials comprising carbon.

5. The gas sensing device according to claim 1, wherein the gas sensing device comprises a processing device comprising a gas concentration estimator comprising a trained model based algorithm processor having an input layer and an output layer, wherein first sensing data derived from the first sensing signals and second sensing data derived from the second sensing signals are fed simultaneously to the input layer, and wherein the concentration of the first gas in the ambient mixture of gases and/or the concentration of the second gas in the ambient mixture of gases are estimated based on output data of the output layer.

6. The gas sensing device according to claim 5, wherein the first chemoresistive gas sensing element, the second chemoresistive gas sensing element and the processing device are arranged at a common substrate.

7. The gas sensing device according to claim 1, wherein the gas filter is implemented as a coating of a gas-sensitive area of the second chemoresistive gas sensing element.

8. The gas sensing device according to claim 5, wherein the gas sensing device comprises a first heating device configured for heating the first chemoresistive gas sensing element and a second heating device configured for heating the second chemoresistive gas sensing element, wherein the processing device comprises a heat control device configured for controlling the first heating device according to a first temperature profile and for controlling the second heating device according to a second temperature device, wherein a maximum temperature of the first temperature profile is lower than a maximum temperature of a second temperature profile.

9. The gas sensing device according to claim 6, wherein the first chemoresistive gas sensing element and the second chemoresistive gas sensing element are arranged at a common side of the common substrate, wherein the processing device is arranged at an opposite side of the common substrate, wherein the first chemoresistive gas sensing element and the second chemoresistive gas sensing element are electrically connected to the processing device by vias.

* * * * *